United States Patent [19]

Brown et al.

[11] Patent Number: 4,594,510
[45] Date of Patent: Jun. 10, 1986

[54] HEAT ENERGY MEASURING SYSTEM

[76] Inventors: Chris W. Brown, 192 Fleetwood Dr., Saunderstown, R.I. 02874; Mark A. Maris, 54 Great Rd., Acton, Mass. 01720; Donald S. Lavery, 4225 Ruskin, Houston, Tex. 77005; Bernard Caputo, Sprucewood Cir., Boxford, Mass. 01921; Mark Model, 31 Englewood Ave., Brookline, Mass. 02146

[21] Appl. No.: 707,265

[22] Filed: Mar. 1, 1985

[51] Int. Cl.[4] .................... G01N 21/31; G01N 21/35; G01N 33/22
[52] U.S. Cl. .................... 250/339; 250/341; 250/343; 374/43
[58] Field of Search .............. 250/339, 343, 340, 341, 250/373, 338 GA; 374/36, 43, 44

[56] References Cited

U.S. PATENT DOCUMENTS 3,896,312 7/1975 Brown et al. .................. 250/343
3,950,101 4/1976 Dewey, Jr. ..................... 356/51
4,102,646 7/1978 Sleeter ........................... 250/338
4,553,032 11/1985 Lo et al. ........................ 250/339

OTHER PUBLICATIONS

Chris W. Brown, "Multicomponent Infrared Analysis Using P-Matrix Methods", *Journal of Testing and Evaluation*, American Society for Testing and Materials, publisher, vol. 12 (Mar. 1984), pp. 86–90.

Mark A. Maris, Chris W. Brown and Donald S. Lavery, "Nonlinear Component Analysis by Infrared Spectrophotometry", *Analytical Chemistry*, vol. 55, No. 11, (Sep. 1983), pp. 1694–1703.

Chris W. Brown, Patricia F. Lynch, Robert J. Obremski and Donald S. Lavery, "Matrix Representations and Criteria for Selecting Analytical Wavelengths for Multicomponent Spectroscopic Analysis", *Analytical Chemistry*, vol. 54, No. 9, (Aug. 1982), pp. 1472–1479.

Primary Examiner—Alfred E. Smith
Assistant Examiner—Constantine Hannaher
Attorney, Agent, or Firm—Joseph S. Iandiorio; William E. Noonan

[57] ABSTRACT

A heat energy measuring system which directs radiation through a sample of a combustible fluid and detects the absorbance of at least one combustible component of the combustible fluid at a selected spectral line, there being at least one spectral line for each combustible component to be examined in the fluid. The system also combines at least one heat energy proportionality factor with the absorbance at each spectral line and sums these combinations to determine the heat energy of the fluid. Where the components to be examined are functional groups, the system measures more generally a physical property of a fluid dependent on the physical characteristics of and the quantity of those functional groups in the fluid.

39 Claims, 8 Drawing Figures

HEAT ENERGY MEASURING SYSTEM

FIELD OF INVENTION

This invention relates to a measurement system for directly quantifying the heat energy of the components of a combustible fluid including functional groups and molecules using spectroscopy and heat of combustion values. The invention relates more generally to the measurement of a physical property of a fluid that is dependent on a physical characteristic of at least one functional group and is related to the quantity of that functional group in the fluid.

BACKGROUND OF INVENTION

Presently, the heat energy or BTU content of a combustible fluid is measured by physically burning precisely defined amounts of the fluid, such as natural gas, to determine the amount of energy produced from the combustion. Other methods measure the concentration of each whole combustible compound in the mixture, defining the energy content for each whole compound, and summing them to yield the heat energy content of the entire mixture.

The heat energy content of natural gas in a pipeline or flowline frequently fluctuates within an hour or less. Natural gas typically contains 60–80% methane, 5–9% ethane, 3–18% propane, and 2–14% higher alkane hydrocarbons. These molecules possess an assortment of $CH_4$ (methane), $CH_3$, $CH_2$, and CH functional groups. Mercaptan odorants, also combustible, are added to provide a distinctive warning odor for reason of safety. Present methods of measurement require bypass flowlines or fluid extraction to provide samples of gas which are taken to a laboratory and burned. The temperature of the flame is then measured. It is difficult to measure the energy content of natural gas in a pipeline both continuously and accurately. Improper charges may result over the course of a day to the disadvantage of both the buyer and seller.

Infrared spectroscopy is one of several types of spectroscopy capable of identifying and quantifying the functional groups of a given compound or mixture as an intermediate step to identifying one or more whole molecules. Infrared radiation causes groups of atoms of organic compounds to vibrate about their covalent bonds. Because of the vibrations, the groups of atoms absorb a quantified amount of infrared energy in particular regions of the spectrum. Each absorptive region is typically specified in frequency units by its wavenumber, measured in reciprocal centimeters. Infrared spectroscopy presently uses many such regions over a spectrum as broad as 200 $cm^{-1}$ to 4000 $cm^{-1}$, since the vibrations result in a variety of stretching and bending of the covalent bonds at different frequencies. The frequency of a given stretching vibration is related to the masses of the bonded atoms and the relative stiffness of the bond.

These mass and bond factors are useful for identifying various hydrocarbons, containing only carbon and hydrogen atoms. A number of absorptive regions are typically examined during the molecule identification process. Carbon-carbon single bonds of alkanes normally give rise to weak absorption peaks that are of relatively little use in identifying compounds. Carbon-carbon double bonds of alkenes provide absorption peaks in the 1620–1680 $cm^{-1}$ region and carbon-carbon triple bonds of alkynes give absorption peaks of approximately 2100–2260 $cm^{-1}$. Carbon-hydrogen stretching vibrations exhibit absorption peaks in the 2800–3300 $cm^{-1}$ region. C—H bonds involving sp-hybridized carbon atoms are stronger than $sp^2$ which are in turn greater in strength than $sp^3$ bonds. The stronger bonds create peaks at higher frequencies.

Infrared spectral information regarding hydrocarbons is therefore used primarily to determine the type of bond between carbon atoms having one or more attached hydrogens for the purpose of separating alkanes, alkenes and alkynes, or for identifying a particular whole hydrocarbon molecule. It is difficult, however, to accurately distinguish between similar hydrocarbons possessing several identical functional groups.

The amount of monochromatic radiation absorbed by a fluid containing a single species is expressed by the Beer-Lambert law $$A = abc$$

where A is the absorbance, a the absorptivity, b the path length or thickness of the sample, and c is the concentration of the species. When the path length is constant, the equation may be written as $$A = kc$$

where a and b are combined to give a single proportionality constant k. Presently the species, or component, whose concentration is to be quantified is a whole molecule.

The relationship of concentration to absorbance at a single analytical frequency can be depicted graphically as a linear function. However, inter- and intramolecular interactions induce deviations from the Beer-Lambert law. A non-zero intercept may be added to approximate non-linear values over a limited region of the curve, giving $$A = k_1 c + k_0$$

where $k_1$, the slope, is the combined proportionality constant and $k_0$ is the non-zero intercept.

The polychromatic radiation used by spectrometers and the chemical interactions among several components in a mixture cause further deviations in the Beer-Lambert law. One derivation of this law utilizes the absorbances of each of n components at several analytical wavelengths to generate simultaneous equations:

$$A_1 = k_{11}c_1 + k_{12}c_2 + \ldots k_{1n}c_n$$
$$A_2 = k_{21}c_1 + k_{22}c_2 + \ldots k_{2n}c_n$$
$$\vdots$$
$$A_n = k_{n1}c_1 + k_{n2}c_2 + \ldots k_{nn}c_n$$

These equations may be expressed in matrix form as $$\begin{bmatrix} A_1 \\ A_2 \\ \vdots \\ A_n \end{bmatrix} = \begin{bmatrix} k_{11} & k_{12} \ldots k_{1n} \\ k_{21} & k_{22} \ldots k_{2n} \\ \vdots & \\ k_{n1} & k_{n2} \ldots k_{nn} \end{bmatrix} \begin{bmatrix} c_n \\ c_n \\ \vdots \\ c_n \end{bmatrix}$$

or

-continued $$A = KC$$

After the K matrix is calculated by measuring the spectra of individual known components, the concentrations of unknown components can be determined from measured absorbances using $$C = K^{-1}A$$

A great disadvantage of this method is that the calculation of the K matrix does not reflect the interactions among molecules. It is known that a mixture of standards provides a more accurate approach. The A and C matrices may be extended to include a column of A's and a column of C's, respectively, for each standard, where each standard contains a mixture of species:

$$\begin{bmatrix} A_1'A_1'' \ldots A_1^m \\ A_2'A_2'' \ldots A_2^m \\ \vdots \\ A_n'A_n'' \ldots A_n^m \end{bmatrix} = \begin{bmatrix} k_{11} k_{12} \ldots k_{1n} \\ k_{21} k_{22} \ldots k_{2n} \\ \vdots \\ k_{n1} k_{n2} \ldots k_{nn} \end{bmatrix} \begin{bmatrix} c_1'c_1'' \ldots c_1^m \\ c_2'c_2'' \ldots c_2^m \\ \vdots \\ c_n'c_n'' \ldots c_n^m \end{bmatrix}$$

$$\overline{A} = K\overline{C}$$

The K matrix is identical to the set of simultaneous equations presented above. Here, $m \geq n$, that is, there must be at least as many standard mixtures as the number of components. Solving for K requires some manipulation: since $\overline{A}$ and $\overline{C}$ are not necessarily square matrices, both sides of the previous equation may be multiplied by the transpose of $\overline{C}$:

$$\overline{AC^t} = \overline{KCC^t}$$

and then the inverse of the square matrix $(\overline{CC^t})$ to yield $$K = \overline{AC^t}(\overline{CC^t})^{-1}$$

representing the least-squares fit of K. However, difficulties arise when a non-zero intercept is added. See Brown, C. W.; Lynch, P. F.; Obremski, R. J.; and Lavery, D. S., "Matrix Representations and Criteria for Selecting Analytical Wavelengths for Multicomponent Spectroscopic Analysis", 54 Anal. Chem. 1472–1479 (1982).

As presented by Brown et al., id., a preferred method of solving for K reverses the Beer-Lambert law to express concentration as a function of absorbance where $$\overline{C} = P\overline{A}$$

or $$\begin{bmatrix} c_1'c_1'' \ldots c_1^m \\ c_2'c_2'' \ldots c_2^m \\ \vdots \\ c_n'c_n'' \ldots c_n^m \end{bmatrix} = \begin{bmatrix} P_{11} P_{12} \ldots P_{1n} \\ P_{21} P_{22} \ldots P_{2n} \\ \vdots \\ P_{n1} P_{n2} \ldots P_{nn} \end{bmatrix} \begin{bmatrix} A_1'A_1'' \ldots A_1^m \\ A_2'A_2'' \ldots A_2^m \\ \vdots \\ A_n'A_n'' \ldots A_n^m \end{bmatrix}$$

The P matrix relates $\overline{C}$ to $\overline{A}$. An additional column may be added to the right-hand side of the P matrix to allow for a non-zero intercept, in which case a last row of 1's is added to the A matrix. P is calculated through the least-squares method, such that $$P = \overline{CA^t}(\overline{AA^t})^{-1}$$

The concentrations of unknowns may also be calculated by $$C = PA$$

See also Brown, C. W., and Lavery, D. S., "Multicomponent Infrared Analysis Using P-Matrix Methods", 12 J. Testing and Eval. 86–90 (1984); Maris, M. A.; Brown, C. W., and Lavery, D. S., "Nonlinear Multicomponent Analysis by Infrared Spectrophotometry", 55 Anal. Chem. 1694–1703 (1983).

As is true for spectroscopy in general, it is still difficult to distinguish between similar molecular components using the P matrix method, particularly when the components have one or more functional groups in common. More fundamentally, the P matrix and spectroscopy are presently directed toward determining the concentration of one or more components, where each component is a species of whole molecule. Physical properties, such as heat energy, that are related to the quantity of certain ingredients in a fluid are viewed in terms of the concentrations of the molecular species. Each molecular species has a known physical characteristic, such as heat of combustion, which is multiplied by the concentration of that species to determine its contribution toward the physical property of the fluid. The physical characteristic of each species must be summed to quantify the total physical property of the fluid. Since there must be at least as many standards as species, and each standard is measured at each wavelength, the calibration process is elaborate and time consuming and the resulting calculations are cumbersome.

SUMMARY OF INVENTION

It is therefore an object of this invention to provide an improved heat energy measuring method and apparatus to quantify the total heat energy of a sample of a combustible fluid.

It is a further object of this invention to provide an energy measurement system which determines the total heat energy without the need for identifying the actual composition of a combustible fluid.

It is a further object of this invention to provide such a system which utilizes the physical relationship between functional groups and their heat energy.

It is a further object of this invention to provide such a system which directly relates absorbance to heats of combustion of functional groups and other components to be examined.

It is a further object of this invention to provide such a system which continuously measures the energy content of a fluid.

It is a further object of this invention to provide such a system which is inexpensive and reliable.

It is a further object of this invention to provide an improved system to measure the energy content of a natural gas mixture in a flow line or chamber.

It is a more general object of this invention to provide an improved method and apparatus for measuring a physical property of a fluid dependent on the physical characteristic of at least one functional group and related to the quantity of that functional group in the fluid.

It is a further object of this invention to provide an improved measuring system which directly relates absorbance to physical characteristics of functional groups to be examined in a fluid.

It is a further object of this invention to provide such a system which obviates the need for identifying the actual composition of the fluid.

This invention results from the realization that, using a derivation of the Beer-Lambert law, a truly effective system for measuring the total heat of combustion of components in a fluid can be achieved by combining at least one heat energy proportionality factor with the absorbance of at least one spectral line for each component to be examined without the need for identifying the actual molecular composition of the fluid.

This invention features a system for measuring the heat energy of a combustible fluid. There is a means for directing radiation through a sample of the fluid and means for detecting the absorbance of at least one combustible component of the combustible fluid at a selected spectral line, there being at least one spectral line for each combustible component to be examined in the fluid. The system also includes means for combining at least one heat energy proportionality factor with the absorbance at each spectral line, and means for summing these combinations to determine the heat energy of the fluid.

In a preferred embodiment, the means for combining includes means for providing the proportionality factors, wherein each heat energy proportionality factor relates one of the absorbances to at least one heat of combustion factor for the heats of combustion of one of each known standard. There are at least as many known standards as the number of combustible components to be examined. Each component has a known heat of combustion, and each known standard includes at least one combustible component.

The means for providing may include a plurality of cells containing each combustible component to be examined in at least one of these cells. Each cell has a known standard which includes at least one combustible component. There may be as many cells as the number of selected spectral lines, and each cell may contain some amount of each combustible component.

The heat energy proportionality factor may be determined from the relationship $$P = \overline{H} A'(\overline{AA'})^{-1}$$

where $P$ is a matrix of heat energy proportionality factors $p_{kj}$, $\overline{A}$ is a matrix of absorbances $A_j{}^i$, $\overline{A'}$ is the transpose of $\overline{A}$, and $\overline{H}$ is a matrix of heat of combustion factors $h_k{}^i$. For these matrices, k indicates one of 1-K combustible components to be examined, j indicates one of 1-N selected spectral lines, and i indicates known standards 1-M. The means for providing may include means for calculating the heat energy proportionality factors and means for storing predetermined heat energy proportionality factors. $\overline{H}$ may be a matrix of heat of combustion factors $h^i$, where i indicates known standards 1-M, and P is a matrix of heat energy proportionality factors $p_j$, where j indicates spectral lines 1-N, and the means for providing provides one proportionality factor for the absorbance at each spectral line.

In one embodiment, the means for determining multiplies each absorbance by the corresponding heat energy proportionality factor, and the means for directing includes means for modulating the radiation, including infrared radiation, at a predetermined frequency and means for synchronizing the detection of absorption with the frequency. The means for detecting measures absorption at at least one additional wavelength at which absorption by the combustible fluid is minimal and detects absorption at at least one spectral line for each $CH_x$ functional group of alkane hydrocarbons to be examined, where x is a number from 1 to 4. The means for detecting may detect functional groups in a sample of combustible gas.

Where the components to be examined are functional groups, the invention more generally features a system for measuring a physical property of a fluid dependent on the physical characteristic of at least one functional group and related to the quantity of that functional group in the fluid. There are means for directing radiation through a sample fluid and means for detecting the absorbance of at least one functional group in the fluid at a selected spectral line, there being at least one spectral line for each functional group to be examined in the fluid. The system also includes means for combining at least one proportionality factor with the absorbance at each spectral line, and means for summing the combinations to quantify the dependent physical property of the fluid.

The means for combining may include means for providing the proportionality factors, wherein each proportionality factor relates one of the absorbances to at least one factor representing the physical characteristics of one of each known standard. There are at least as many standards as number of functional groups to be examined. Each functional group has a known physical characteristic and each known standard includes at least one functional group. Other aspects of this embodiment are similar to those described for the heat energy measuring system.

The invention further encompasses methods for measuring the heat energy or other physical property of a fluid dependent on the physical characteristic of at least one functional group and related to the quantity of that functional group in the fluid. The method for measuring the heat energy includes directing radiation through a sample of the fluid, selecting at least one spectral line for each combustible component to be examined, and detecting the absorbance of at least one combustible component of the fluid at each selected spectral line. The method further includes providing a heat energy proportionality factor between the absorbance at each selected spectral line and a heat of combustion factor for a known standard including at least one combustible component to be examined, there being at least one known standard for each combustible component. The method also includes combining each heat energy proportionality factor with the absorbance of each spectral line, and summing the combinations to determine the heat energy of the combustible fluid. The method of measuring a dependent physical property is similar to the method of measuring heat energy.

DISCLOSURE OF PREFERRED EMBODIMENT

Other objects, features and advantages will occur from the following description of a preferred embodiment and the accompanying drawings, in which.

Unlike previous devices, a heat energy measuring system according to this invention relates absorbance directly to the heats of combustion of functional groups and other combustible components selected for measurement in a combustible fluid. The measuring system need not determine the actual molecular composition of the fluid. Rather than determine the concentration of each species of compound as a step toward measuring the heat energy of a fluid, the system takes advantage of the known amounts of energy stored in the atomic bonds of a given species of functional groups which may be found in one or more compounds within the fluid. That is, the system utilizes the heat energy of functional groups as represented by a heat of combustion value for each type of functional group. The heat energy of the fluid is the absolute or relative heat of combustion value for that fluid.

A heat energy measuring system according to this invention may also view a combustible fluid in terms of whole molecules: not to determine concentration, but to directly determine the heat energy contribution of each combustible component. This is accomplished using heat energy proportionality factors which relate the absorbance of the fluid at each selected spectral line to heat of combustion factors, as described below. The term "combustible component" refers to a discrete constituent, such as a functional group or a whole molecule, which has a known physical characteristic, such as heat of combustion, per unit quantity.

Figure 1:
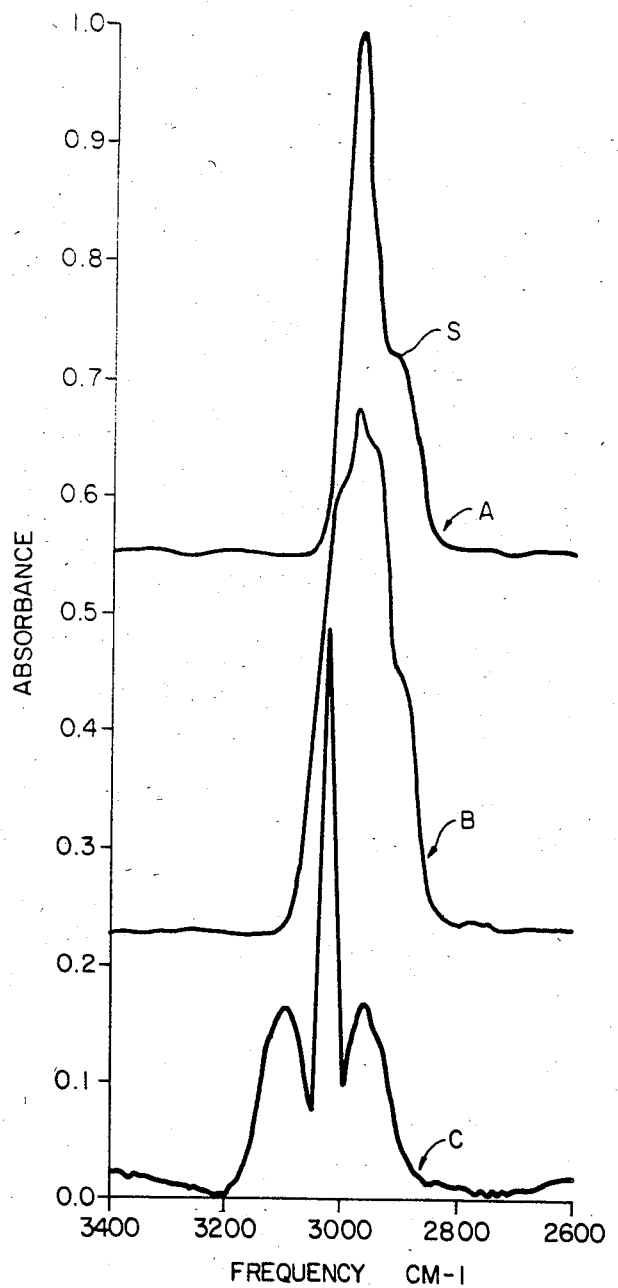
FIG. 1 is a graph of absorbance versus frequency for three alkane hydrocarbons.

The difficulty of distinguishing three similar hydrocarbons is indicated in FIG. 1 by the similar absorbance patterns of propane, spectrum A, ethane, spectrum B, and methane, spectrum C. All carbon-hydrogen molecules strongly absorb infrared radiation in the spectral region of approximately 3.3 microns. Spectra A through C, shown with flattened baselines, represent absorbance measurements at a wavelength resolution of 25 cm$^{-1}$; spectrum C has been expanded 5X and smoothed for clarity. These typical spectra represent 173 parts per million (ppm) of propane, 432.5 ppm ethane, and 216.2 ppm methane. The central peak in spectrum C for methane appears at 3020 cm$^{-1}$ (3.31 microns) whereas the central absorption in spectra A and B of propane and ethane are approximately 2970 cm$^{-1}$ (3.37 microns). Shoulder S in spectrum A, located at approximately 2930 cm$^{-1}$ (3.41 microns), is due to the $CH_2$ functional group of propane.

The absorption frequencies of $CH_x$ functional groups are independent of the particular molecules contained in these groups, and the magnitude of the absorption at each frequency is dependent on the number of groups absorbing at a given frequency. For hydrocarbons, heat is produced when carbon and hydrogen atoms combine with oxygen during combustion. As shown in Table I, the heat combustion for alkane hydrocarbons display a useful relationship between molecular structure and heat energy. For unbranched low-molecular-weight hydrocarbons, the heat of combustion increases by approximately 158 kcal/mole for each additional $CH_2$ group, as shown in the fourth column of Table I.

TABLE I

Heats of Combustion for Alkane Hydrocarbons.

| Chemical | Structure | kcal/mole | kcal/$CH_2$ | kcal/gram | BTU/lb |
|---|---|---|---|---|---|
| methane | $CH_4$ | 212.95 | | 13.30 | 23,961 |
| ethane | $CH_3CH_3$ | 373.1 | | 12.44 | 22,405 |
| | | | 158.7 | | |
| propane | $CH_3CH_2CH_3$ | 531.8 | | 12.10 | 21,691 |
| | | | 157.3 | | |
| n-butane | $CH_3(CH_2)_2CH_3$ | 689.1 | | 11.88 | 21,402 |
| | | | 158.0 | | |
| n-pentane | $CH_3(CH_2)_3CH_3$ | 847.1 | | 11.77 | 21,204 |
| | | | 158.5 | | |
| n-hexane | $CH_3(CH_2)_4CH_3$ | 1005.6 | | 11.69 | 21,060 |
| | | | 157.2 | | |
| n-heptane | $CH_3(CH_2)_5CH_3$ | 1162.8 | | 11.62 | 20,934 |
| | | | 157.8 | | |
| n-octane | $CH_3(CH_2)_6CH_3$ | 1320.6 | | 11.58 | 20,862 |
| i-butane | $(CH_3)_2CHCH_3$ | 687.0 | | 11.84 | 21,339 |
| i-pentane | $(CH_3)_2CHCH_2CH_3$ | 845.0 | | 11.73 | 21,144 |
| i-hexane | $(CH_3)_2CH(CH_2)_2CH_3$ | 1003.2 | | 11.67 | 21,025 |
| 2-methylhexane | $(CH_3)_2CH(CH_2)_3CH_3$ | 1161.4 | | 11.61 | 20,916 |
| 2-methylheptane | $(CH_3)_2CH(CH_2)_4CH_3$ | 1319.0 | | 11.57 | 20,845 |
| 2,3-dimethylbutane | $(CH_3)_2CHCH_3CHCH_2CH_3$ | 1160.4 | | 11.60 | 20,906 |
| 2,5-dimethylhexane | $(CH_3)_2CH(CH_2)_2CH(CH)_3$ | 1317.3 | | 11.56 | 20,818 |

The heat of combustion is linearly related to the number of $CH_x$ functional groups present. For example, a mixture of one mole of butane and one mole of hexane has the same heat of combustion as that of two moles of pentane. Heat energy systems according to this invention utilize the direct relationship between heat of combustion and the relative quantities of $CH_4$, $CH_3$, $CH_2$, and CH in a fluid.

Other functional groups may be examined in the same manner. Ethyl mercaptan is frequently used as an odorant in natural gas. It has a structure of $CH_3CH_2SH$ and is combustible. The SH functional group has an absorbance peak at 2600 cm$^{-1}$ (3.8 microns). Alcohols contain an OH functional group which has an absorbance peak of 3700 cm$^{-1}$ (2.7 microns). Functional groups identical to others to be examined, such as $CH_3$ and $CH_2$, are accounted for at their respective spectral lines. Other functional groups, such as SH or OH, provide absorbance peaks at additional spectral lines which may then be related to known heats of combustion for these differing groups.

Figure 2:
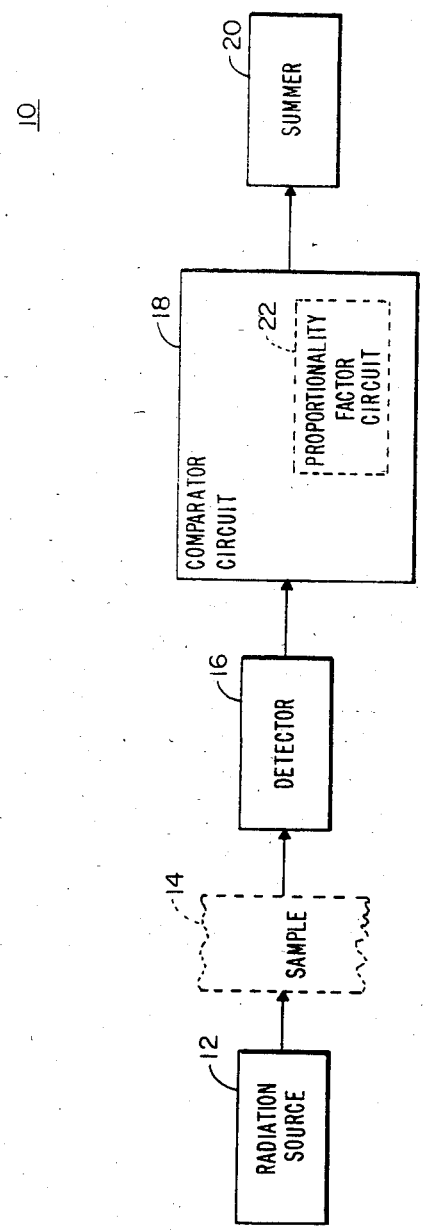
FIG. 2 is a schematic block diagram of a heat energy measuring system according to this invention.

Heat energy measuring system 10, FIG. 2, includes radiation source 12 which passes radiation through sample 14, shown in phantom. Sample 14 contains a combustible fluid containing at least one combustible component to be examined. Radiation source 12 emits a sufficient spectra of continuous or modulated radiation such that there is at least one spectral line for each combustible component to be examined. Detector 16 detects the absorbance of the combustible components at the selected spectral lines, and transfers this information to comparator circuit 18. Comparator circuit 18 combines at least one heat energy proportionality factor with each absorbance. These combinations are summed by summer 20 to determine the total heat energy of the combustible fluid.

Comparator circuit 18 may include proportionality factor circuit 22, shown in phantom, which stores predetermined heat energy proportionality factors or calculates the proportionality factor as described below. The circuits may be implemented in hardware or software.

Figure 3:
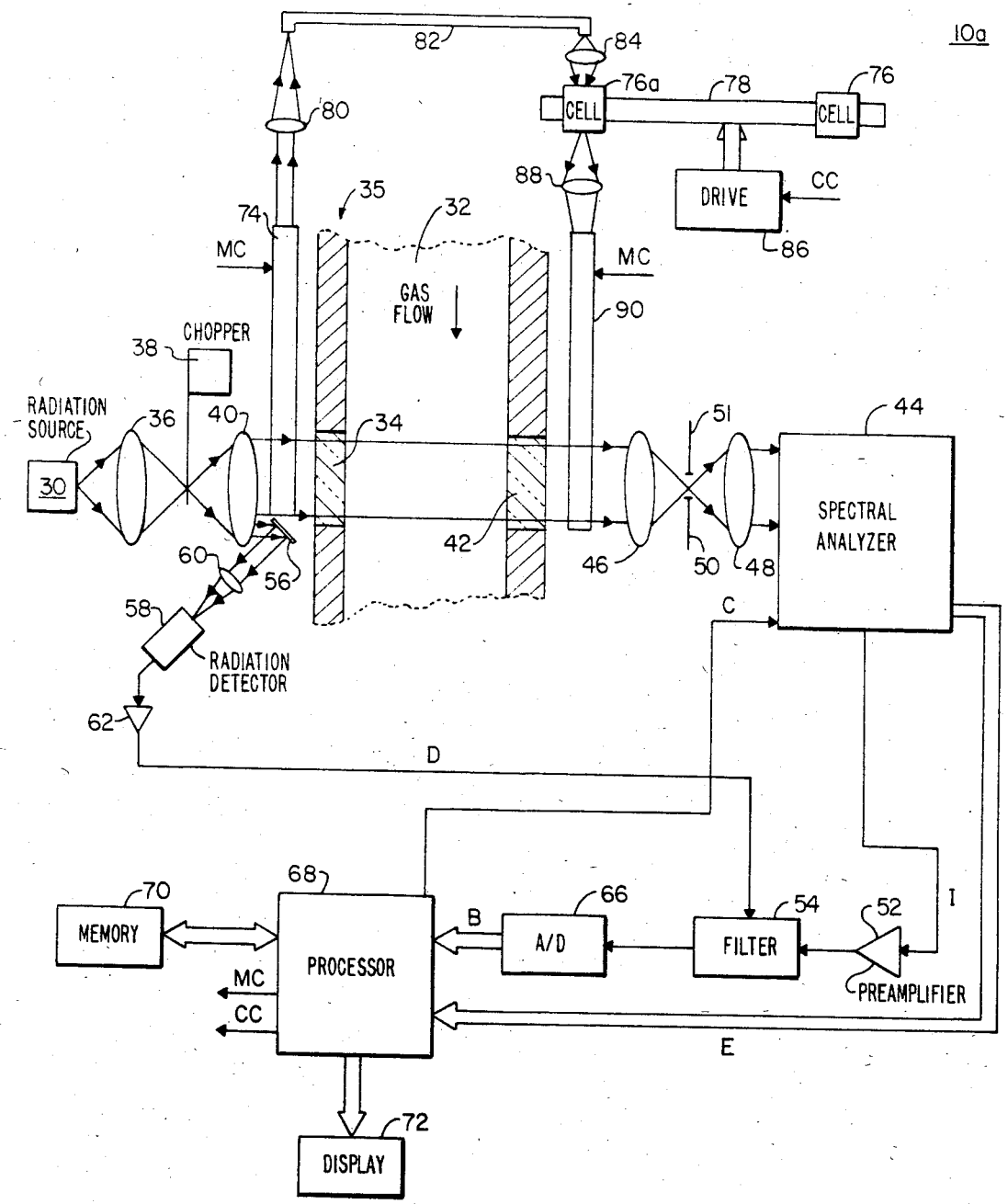
FIG. 3 is a more detailed schematic of a measuring system according to this invention.

Heat energy measuring system 10a utilizing infrared spectroscopy is shown in FIG. 3. Radiation source 30 emits a plurality of wavelengths, some of which are absorbed by the $CH_x$ functional groups and other combustible components of fluid 32. Radiation source 30 may be a broad band source of radiation, such as a tungsten lamp, or several narrow band sources, such as a plurality of lasers. For examining hydrocarbons, radiation source 30 emits infrared radiation including wavelengths between 3.0-3.5 microns. The radiation is modulated and directed through sight window 34. In one embodiment, this is accomplished by focussing radiation through lens 36 to chopper wheel 38 and lens 40. Chopper wheel 38 interrupts the radiation at a predetermined frequency, typically 1-2 $KH_z$; alternatively, radiation source 30 is internally modulated. Chopper wheel 38 is a disc with holes set at known intervals to interrupt the radiation beam, or may be a piezoelectric interrupter, an accousto-optical interrupter, or other device for modulating the beam at a known frequency. The radiation beam is directed through sight window 34 of chamber 35 to sight window 42. The radiation makes a single pass through fluid 32, although multipath arrangements may also be used. The beam is focussed and directed to spectral analyzer 44 through lenses 46, 48, and slit 50 of partition 51.

Analyzer 44, described below, provides signal E, representing the wavelength analyzed at a particular moment in time, and signal I, corresponding to the intensity of radiation transmitted at that wavelength. Signal I is an analog signal representing the magnitude of absorption. Signal E is a digital signal representing the wavelength.

Signal I is amplified by pre-amplifier 52 and rectified by filter 54. A lock-in amplifier is preferred for its more narrow filtering. One such lock-in amplifier is model No. 5101, available from EG&G Princeton Applied Research. Accurate filtering of signal I is obtained by synchronizing lock-in amplifier 54 with the frequency of the radiation beam, represented by signal D. Signal D is obtained by reflecting a portion of the beam passing through lens 40 from mirror 56 into radiation detector 58 through lens 60. Detector 58 provides a signal D, amplified by amplifier 62, which is provided in analog form to lock-in amplifier 54. Filtered and rectified signal I is digitized into digital signal B by A-D converter 66 and provided to processor 68. The logic performed by processor 68 and its interaction with memory 70 is described below. The output is presented in display 72.

Prior to monitoring, the measuring system must be calibrated for the functional groups and other components to be examined. As described below, the P matrix method may be used to develop the proportionality factor between absorbance and the heats of combustion of the combustible components in the fluid. The P matrix must be calculated before monitoring, and may be calculated at intervals during monitoring. The spectral distribution and intensity of radiation from radiation source 30 may change over time, and the system electronics may vary.

To compensate for periodic misalignments, measuring system 10a includes elements for providing periodic calibration. Optical switch 74, such as a mirror or a beam splitter, diverts all or a known fraction of the radiation from the path through sight glass 34 when commanded by processor 68 through signal MC and conveys that radiation to sample cells 76 in cell wheel 78. This may be accomplished using optical switch 74 to pass radiation through lens 80 to optical link 82, such as fiber optics or other means of conveying the radiation. The diverted radiation then passes through lens 84 to the set of cells 76. Drive motor 86, as commanded by signal CC from processor 68, positions, for example, cell 76a in the path of the diverted radiation.

Cells 76 contain known quantities of functional groups or other components with a known physical characteristic identical to that of the property to be monitored in the fluid. More specifically, cell 76a contains at least one component which may be present in the combustible fluid. Cell wheel 78 contains at least as many sample cells as components to be identified. Each of these components must appear at least once in one cell. Typically two or more functional groups are present in each cell, since these functional groups comprise discrete molecules. To account for the interactions among components, mixtures of components are desired: each cell may contain some amount of each combustible component to be examined.

An additional empty cell provides the transform of the system by indicating the loss in transmission not attributable to absorbance by fluid in the cells. The signal produced by the empty cell is designated $I_0'$. A separate $I_0'$ may be used for monitoring as described below.

Radiation is absorbed according to the type and quantities of the components of cell 76a. The remaining radiation passes through lens 88 to optical switch 90, also comanded by signal MC, where it is diverted through lenses 46 and 48, and slit 50 to spectral analyzer 44.

Although the calibration elements of measurement system 10a periodically interrupt monitoring to provide calibration, a two-channel system can be achieved by modulating the diverted radiation at a second frequency. For example, a chopper wheel may be placed between lens 80 and optical link 82. Optical switch 74 can be placed before chopper 38 and an arrangement similar to mirror 56, detector 58 provides frequency information from this second channel to filter 54. Signals I and E produced by the diverted radiation having a second frequency are then distinguished at filter 54 from signals I and E produced by radiation, having a first frequency, which simultaneously passes through chamber 35. Optical switches 74, 90 remain in place to divert a portion of the radiation beam; alternatively, optical switches 74 and 90 may be beam splitters.

Variations in radiance output and actual transmission through sight windows 34 and 42 can change over time through accumulation of dust. Transmission through fluid 32 itself can change through changes in concentration and sizes of particles or through the introduction of impurities. To compensate for the change in transmittance independent of the combustible content of the fluid mixture, absorption at one or more wavelengths not absorbed by the combustible ingredients of the fluid mixture are also measured. Each absorbance at a particular spectral line has a normalizing constant $Kj_{norm}$. The constant is the reciprocal of transmission at a nonsorptive wavelength located near the frequency of the absorptive spectral lines. One constant may be used for $CH_x$ at the higher wavelength of 3.5 microns.

Figure 4A:
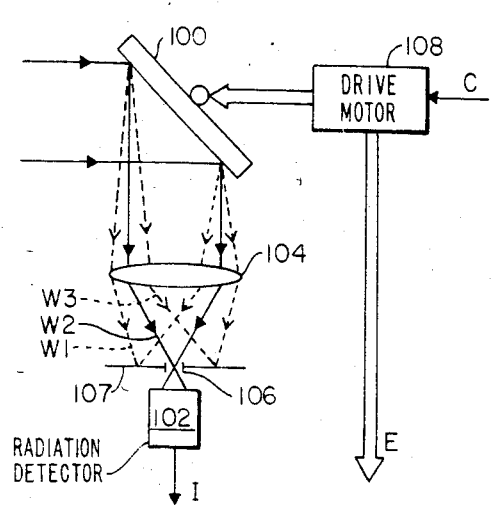
FIGS. 4A-4C are more detailed schematics of the spectral analyzer of FIG. 3.
Figure 4B:
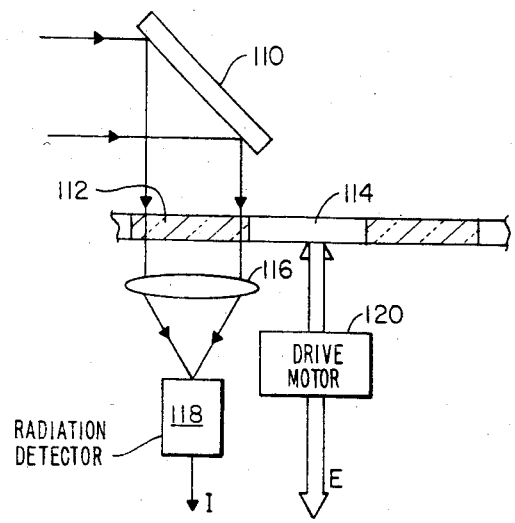
Figure 4C:
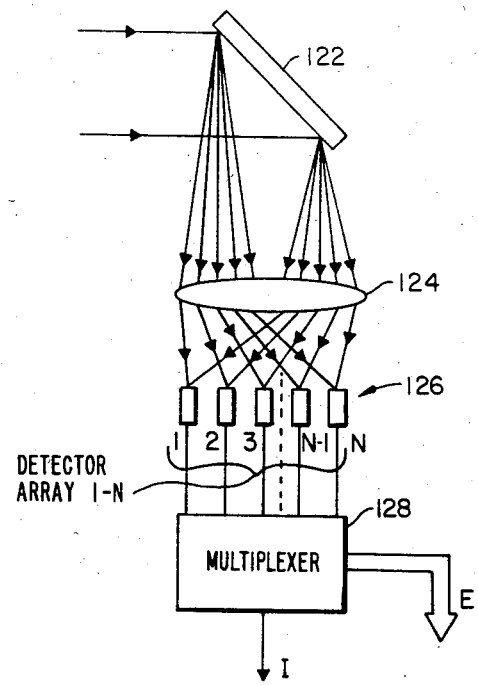

The operation of spectral analyzer 44 is controlled by processor 68 through signal C. Several types of spectral analyzers are shown in FIGS. 4A, 4B, and 4C. The beam transmitted through fluid 32 is received by dispersive element 100, FIG. 4A, such as a dispersive prism or diffraction grating to decompose the radiation into a continuous spectrum represented by wavelength paths W1, W2, and W3. A discrete wavelength W2 is provided to radiation detector 102 through lens 104 and slit 106 in partition 107 by the positioning of dispersive element 100 by drive 108. Signal E representing the distinguished wavelength received by radiation detector 102, W2 in this example, is provided by the action of drive motor 108 on dispersive element 100 as commanded by signal C. Signal I is provided by the output of detector 102.

Alternatively, mirror 110, FIG. 4B, directs radiation through filters 112 of filter wheel 114. The wavelength passing through filter 112 is collected by lens 116 and directed to radiation detector 118. Filter wheel 114 has a set of N filters 112 corresponding to the N wavelengths of interest. Signal I is emitted from detector 118, and signal E is obtained from the position of filter wheel 114 as determined from drive motor 120. Instead of filter wheel 114, a continuous filter wedge can be used.

In another embodiment, FIG. 4C, dispersive element 122 provides a spectrum of radiation through lens 124 to an array of detectors 126. Array 126 contains N detectors, corresponding to the N wavelengths to be distinguished and measured. Multiplexer 128 provides a single output as signal I corresponding to the output of one detector in array 126, and provides signal E representing the detector generating signal I, and thus representing that distinguished wavelength.

Measuring system 10a utilizes the P-matrix method. This method, developed for performing a least squares regression analysis of calibration data from multicomponent spectral analysis, is presently used to obtain concentrations of unknowns in a sample using absorbances measured at several spectral lines. Rather than identifying and quantifying the concentration of entire molecules, measuring system 10a uses the P-matrix to directly determine the heat energy of an unknown fluid by determining the heat of combustion of the fluid as a whole. The heat of combustion of the combustible component in the fluid can be directly related to the infrared absorption spectra by $$H = PA \tag{1}$$

or $$\begin{bmatrix} h_1 \\ h_k \\ \cdot \\ \cdot \\ h_k \end{bmatrix} = \begin{bmatrix} p_{11} p_{12} \cdots p_{1N} \\ \cdot \\ \cdot \cdot p_{kj} \cdot \\ \cdot \\ p_{k1} p_{k2} \quad p_{kN} \end{bmatrix} \begin{bmatrix} A_n \\ \cdot \\ A_j \\ \cdot \\ A_N \end{bmatrix} \tag{2}$$

where H is the heat of combustion matrix, $h_k$ is the heat of combustion for k combustible components 1-K, A is the absorbance matrix, $A_j$ is the absorbance of j spectral lines 1-N, and P is the proportionality matrix of heat energy proportionality constants $p_{kj}$. During the calibration procedure, presented below, the P matrix can be determined by the least squares approach as $$P = \bar{H}\bar{A}^t(\bar{A}\bar{A}^t)^{-1} \tag{3}$$

where $$P = \begin{bmatrix} p_{11} & p_{12} & \cdots & p_{1N} \\ p_{21} & p_{22} & \cdots & p_{2N} \\ \cdot & \cdot & p_{kj} & \cdot \\ \cdot & & & \cdot \\ \cdot & & & \cdot \\ p_{N1} & p_{N2} & \cdots & p_{NN} \end{bmatrix} \tag{4}$$

$$\bar{A} = \begin{bmatrix} A_1^1 & A_1^2 & \ldots & A_1^M \\ A_2^1 & A_2^2 & \ldots & A_2^M \\ \cdot & \cdot & A^j & \cdot \\ A_N^1 & A_N^2 & \ldots & A_N^M \end{bmatrix} \tag{5}$$

$$\bar{H} = \begin{bmatrix} h_1^1 & h_1^2 & \ldots & h_1^M \\ h_2^1 & h_2^2 & \ldots & h_2^M \\ \cdot & \cdot & h_k^i & \cdot \\ h_k^1 & h_k^2 & \ldots & h_k^M \end{bmatrix} \tag{6}$$

Known standards 1-M are indicated by i, which identifies the columns of the $\bar{A}$ and $\bar{H}$ matrices. Components 1-K lie in the rows of matrices P and $\bar{H}$. Spectral line 1-N identify the row of $\bar{A}$ and the column of P. The number N of analytical wavelengths at which absorbance is measured is equal to or greater than the number K of heats of combustion. The number M of known standards is equal to or greater than the number N of spectral lines. Thus $$M \geq N \geq K \tag{7}$$

$A_j$, and therefore $A^t$, are determined by measuring the absorbance at each wavelength j for each known standard i. Each standard has a known quantity of one or more combustible components, each component having a known heat of combustion. $\bar{H}$ is generated by summing the known heat of combustion for each combustible component to determine the total heat of combustion value for that standard. The heat of combustion value is related to absorbance by the proportionality constant $p_{kj}$.

During calibration, each row of the P matrix is determined independently of every other row. Where one physical property, such as heat energy, may be used to describe all the constituents of a fluid, that property can be expressed in matrix form as abbreviated matrices.

$$h = [p_1 p_2 \ldots p_j \ldots p_N] \begin{bmatrix} A_1 \\ A_2 \\ \cdot \\ \cdot \\ \cdot \\ A_j \\ A_N \end{bmatrix} \quad (8)$$

or $$h = \sum_{j=1}^{N} p_j A_j \quad (9)$$

where h is the heat of combustion of the entire fluid, $A_j$ the absorbance at the jth spectral line, and $p_j$ is the respective proportionality factor. When solving for P during calibration, equation 3, the abbreviated P matrix becomes $$P = [p_1 p_2 \ldots p_N] \quad (10)$$

and the abbreviated $\overline{H}$ matrix becomes $$H = [h_1 h_2 \ldots h_N] \quad (11)$$

In other words, k=1.

The abbreviated matrix method and the full matrix method require the same minimum number of known standards. There are at least as many standards as the number of combustible components to be examined. The difference between the methods lies in the separate treatment in the full matrix method of each individual heat of combustion value for each component within a standard. The abbreviated method simply uses one heat of combustion value for the standard, thus drastically reducing the matrix calculations.

Where the relationship between the physical property and absorbance is non-linear such that deviations from the linear Beer-Lambert law are great, it is desirable to manipulate absorbance values more exhaustively, requiring a P-matrix derived from a higher order equation. One such higher order equation is the quadratic equation. When two highly non-linear components are to be examined, the quadratic equations are:

$$h_1 = p_{11}A_1 + p_{12}A_2 + p_{13}A_1{}^2 + p_{14}A_2{}^2 + p_{15}A_{12}$$

$$h_2 = p_{21}A_1 + p_{22}A_2 + p_{23}A_2{}^1 + p_{24}A_2{}^2 + p_{25}A_{12} \quad (12)$$

where $h_1$ and $h_2$ provide the total heat of combustion H for the two-component fluid, the third and fourth terms in the equation are the square terms, and $p_{15}A_1A_2$ and $p_{25}A_1A_2$ are the cross terms. In relation to equation 2, the P matrix is increased by K(K+1)/2 columns and the A matrix is increased by K(K+1)/2 rows of square and cross terms. Unless there is strong interaction between the components, the cross terms can be omitted to provide power series equations. The P matrix is thereby increased by K columns and the A matrix by K rows. The number of known standards required for the quadratic expression is:

$$M = N + K(K+1)/2 \quad (13)$$

and for the power series is $$M = N + K \quad (14)$$

The use of higher order equations such as quadratic and power series equations noticeably improves the accuracy and fit of the information derived from the standards during the calculation of the P matrix. As is evident from equations 12-14, however, calibration using higher order equations increases tremendously the complexity and computing time required to solve for the P matrix.

Figure 5:
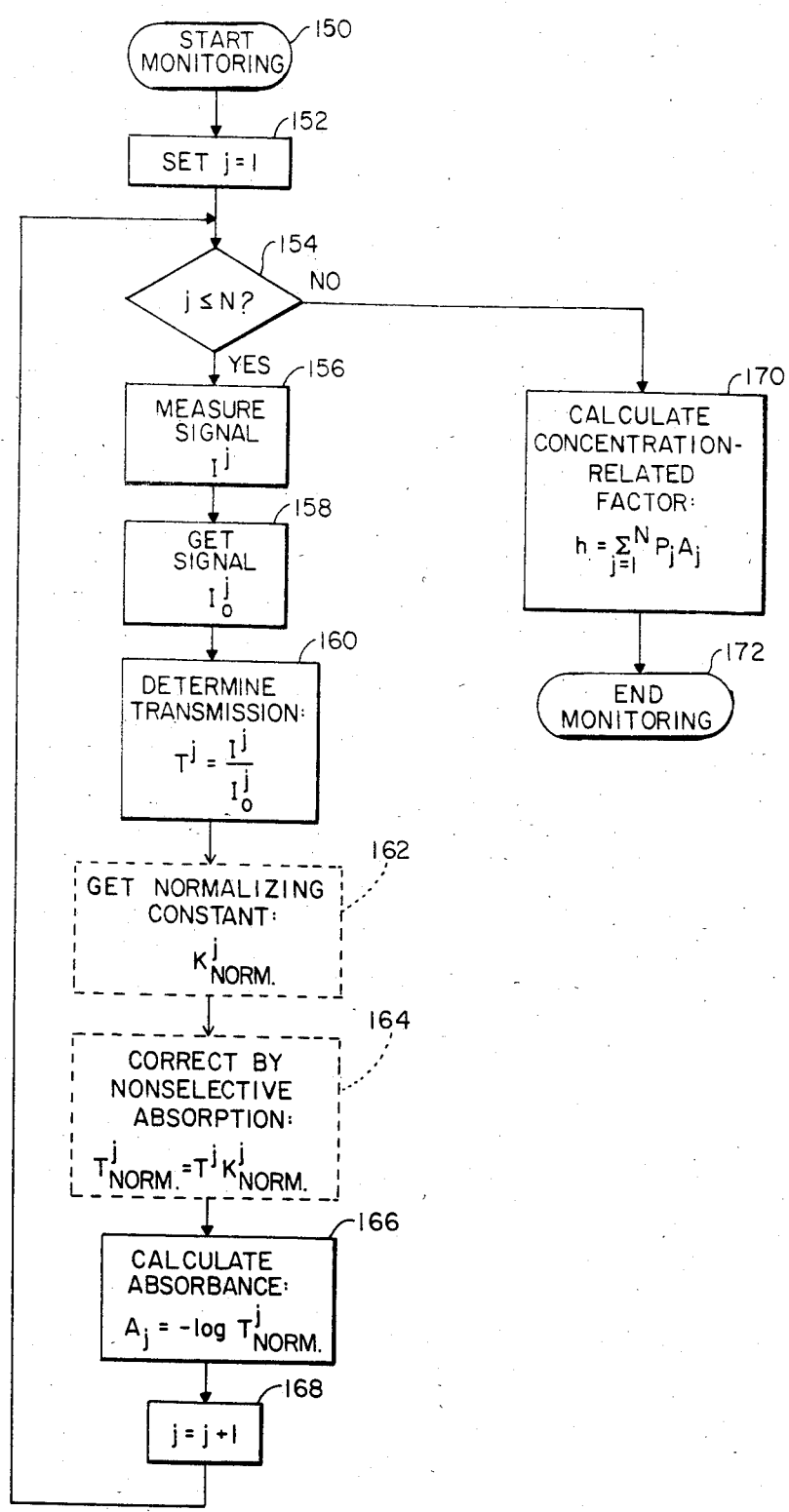
FIG. 5 is a flow chart of the monitoring process conducted by the measuring system of FIG. 3.

The measurement procedure performed by measuring system 10a is depicted in FIG. 5. When monitoring begins, step 150, the wavelength j is set to 1, step 152, as commanded by processor 58, FIG. 3, through signal C to spectral analyzer 44. Wavelength index j indicates the selected spectral lines for the components to be identified, and additional nonabsorptive spectral lines if desired. At step 154, FIG. 5, if j is less than or equal to N, where N is the final spectral line to be detected, signal $I^j$ is measured at step 156. Signal $I_0{}^j$, obtained from the memory during step 158, is divided into signal $I^j$ to determine actual transmission, step 160.

$I_0{}^j$ for monitoring can be derived using several different methods. If the optical parameters, such as aperture, path length, and field of view, of the calibration and monitoring radiation channels are equivalent, the $I_0{}^j$ obtained during calibration can be used in step 158. If the optical parameters are not equal, the calibration $I_0{}^j$ can still be used: it accounts for changes in the spectral distribution of the source radiation and $K_{norm}{}^j$, described below, accounts for changes in output intensity of the radiation source.

Alternatively, proportionality constants $\epsilon_0{}^j$ can be calculated or experimentally obtained before installation or before introducing the combustible fluid to be monitored into the flow line or chamber. The $\epsilon_0{}^j$ are given by:

$$\epsilon_0{}^j = \frac{I_0{}^j mon}{I_0{}^j cal}$$

where $I_0{}^j cal$ is the signal produced by the empty cell in the cell wheel at the j-th wavelength, and $I_0{}^j mon$ is the signal produced by the empty chamber or flow line at the j-th wavelength. For every given cell size there are as many sets of $\epsilon_0{}^j$ as the number of different sizes of the flow lines to be monitored. One or more of these $\epsilon_0{}^j$ are stored, depending upon the application of the measuring system. At step 158, all the $I_0{}^j$ are then the product of $I_0{}^j cal$ multipled by $\epsilon_0{}^j$, where $I_0{}^j cal$ are obtained at calibration.

$I_0{}^j$ can also be defined directly in the monitoring channel by periodically stopping the flow through the line or emptying the chamber, then measuring the $I_0{}^j$ and storing them in the memory. In yet another arrangement, a third channel is utilized which has optical characteristics equivalent to the monitoring channel. A beam splitter or multiplexer is installed before and after the flow line to direct some or all of the radiation through the third channel. $I_0{}^j$ can thereby be obtained before every monitoring measurement or as often as desirable.

If desired, transmission $T^j$ can be corrected by obtaining normalizing constant $K^j norm$, step 162, which is mutiplied by $T^j$ to provide $T^j{}_{norm}$, step 164. $K^j{}_{norm}$ is the reciprocal of transmission at a nonsorbtive wavelength, as described above. The absorbance is then calculated by taking the negative log of $T^j{}_{norm}$ to obtain absorbance $A_j$, step 166. Wavelength j is incremented by one, step 168, and the loop returns to decision point 154. Once absorbances have been calculated for all spectral lines, the concentration related factor $\overline{H}$ is calculated, step 170. Step 170 depicts calculations using the abbreviated matrices as described above. Alternatively the system solves for the full H matrix. The heat of combustion h equals the sum of proportionality factor $p_j$ multiplied by absorbance $A_j$ for spectral lines 1-N. h represents the total heat of combustion, or heat energy, of the unknown fluid, thus completing the monitoring procedure, step 172.

Instead of measuring total heat energy, the measuring system can determine relative heat energy such as kcal/mole or other unit. For relative measurements all absorbances during monitoring and calibration are normalized to the absorbance at a chosen wavelength such that $$A_{j\,norm} = A_j/A_{j\,chosen} \quad (16)$$

$A_{jnorm}$ is then used in place of $A_j$ in step 170.

The chosen wavelength should be one that is absorbed to some degree by the fluid to be examined. For most hydrocarbons, a desirable wavelength is one that is absorbed by $CH_3$. It is also desirable that $A_{j\,chosen}$ be linearly related to the heat energy or other physical property to be measured in the range of the Beer-Lambert law or its derivation used during calculation for both monitoring and calibration.

Figure 6:
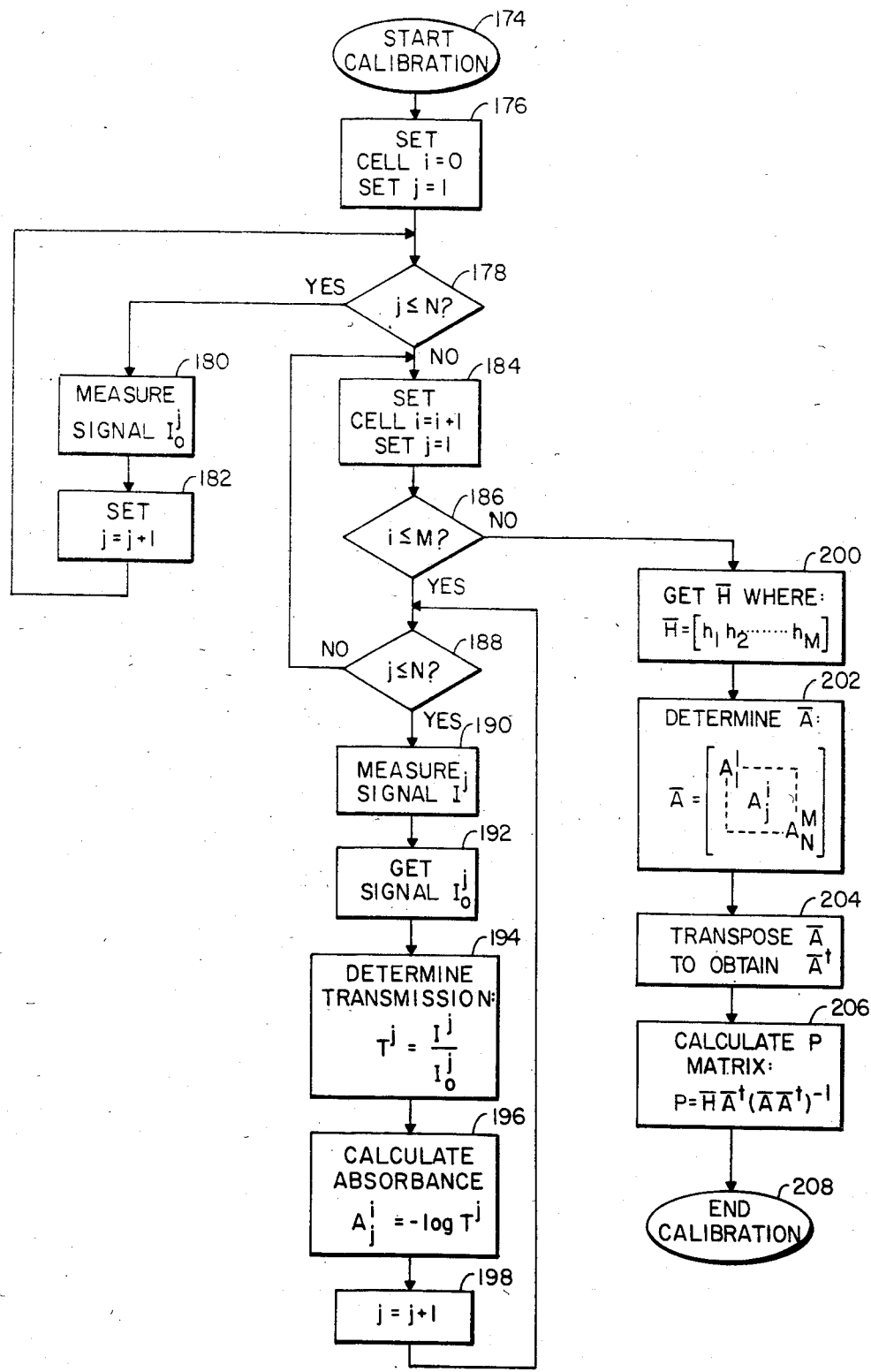
FIG. 6 is a flow chart of the calibration procedure for the system of FIG. 3.

The procedure for calibration is shown in FIG. 6. When calibration is desired, step 174, the sample cells of cell wheel 78, FIG. 3, are set so that the empty cell is positioned between lenses 84, 88. The empty cell, number zero, is designated in step 176. Wavelength index j is set to one. Next, all selected spectral lines 1-N are sequentially passed through cell number zero, as indicated by decision point 178 and operations 180, 182, as the respective intensities $I_0{}^j$ are measured.

After all transformed signals $I_0{}^j$ have been attained, the next sample cell is positioned, step 184. While i is less than or equal to M, step 186, and wavelength j is less than or equal to N, step 188, the absorbance for sample i at wavelength j is calculated in steps 190, 192, 194, and 196. Wavelength index j is incremented by one, step 198, and decision point 188 is reached again. After all samples 1-M have been analyzed, step 200 is reached from decision point 186. As described above, the $\overline{H}$ matrix is obtained from memory. The $\overline{H}$ matrix may be a square matrix where each $h_k{}^i$ represents the heat of combustion of a particular combustible component. Alternatively, $\overline{H}$ may be a single row matrix, where each $h^i$ represents the entire heat of combustion for each known standard 1-M. At step 202, the $\overline{A}$ matrix is determined from the $A_j{}^i$ which were measured in the steps above. The $\overline{A}^t$ matrix is obtained by transposing $\overline{A}$, step 204. The P matrix is then calculated, step 206, to determine each $p_{kj}$ or each $p_j$. Calibration is completed at this point, step 208.

The difference in path length between the calibration cell and the flow line sample to be measured does not affect calculations where the relationship between the physical property and absorbance is linear. When deviations from the Beer-Lambert law are great and the path lengths are not equal, the calibration procedure must take into account the path length difference. This may be accomplished by measuring two A matrices, one for the calibration cell set and the other for a cell set of known standards having a path length equal to that of the flow line. From these two A-matrices a correction matrix L can be calculated as $$L = \begin{bmatrix} l_{11} & \cdots & l_{1N} \\ & \cdot & \\ \cdot & l_{kj} & \cdot \\ & \cdot & \\ l_{K1} & \cdot & l_{KN} \end{bmatrix} \quad (17)$$

where the correction coefficient $l_{kj}$ is determined from $$l_{kj} = A_{kj}{}^{mon}/A_{kj}{}^{cal} \quad (18)$$

wherein $A_{kj}{}^{mon}$ are the absorbances measured on the second set of cells when placed into the flow line path and $A_{kj}{}^{cal}$ are the absorbances measured on the calibration cell set. This L-matrix is stored in the memory. The A matrix actually used in calibration, step 202-206, is obtained by multiplying each $A_{kj}{}^{cal}$ by its respective $l_{kj}$ to yield $A_{kj}{}^{mon}$. Thus the P-matrix for the solution of the equations 8 or 9 is calculated with this new A matrix. The L matrix for all potential path lengths can be determined and be available from the memory as needed or only the L matrix necessary for the particular flow line path length can be used.

Although the system according to this invention is described and titled as a heat energy measuring system, this is not a limitation of the invention. Any physical property which is dependent on the physical characteristic of one or more functional groups and related to the quantity of those functional groups can be measured using a system according to this invention. The measuring system directly relates the physical property to absorbance using predetermined proportionality factors, following the same procedures as described above for measuring heat energy using heat energy proportionality factors. For example, total molecular weight, or other thermodynamic properties such as heat of vaporization, thermal conductivity, or heat capacity of a fluid could be measured. As shown in FIG. 2, comparator circuit 18 would combine proportionality factors, such as those provided by proportionality factor circuit 22 from calibrations according to the procedure outlined in FIG. 6, with the absorbance at each selected spectral line of the fluid whose physical property is to be measured.

As a physical property measuring system, system 10a, FIG. 3, provides intensity signal I representing absorption of the fluid to be measured. Signal E represents the wavelength at which absorption occurred. Cell wheel 78 includes standards containing a known quantity of at least one functional group to be examined, each functional group having a known physical characteristic on which the physical property depends.

The P matrix as used in equation 1 expresses the relationship between the physical property, such as molecular weight, that is dependent on the physical characteristics of certain functional groups and the absorbance of the fluid. H becomes a matrix of physical property values representing the quantity of that physical property in the fluid. Using the abbreviated matrix method, equation 8, the physical property is expressed in a single value h. During calibration, where the P matrix is calculated according to equation 3, $\overline{H}$ is a matrix of physical characteristic factors $h_k{}^i$, such as the molecular weight of the $k^{th}$ functional group in the $i^{th}$ standard. As indicated in equations 10 and 11, k=1 for $h_k{}^i$ and $p_{kj}$ when the abbreviated matrix method is used;

physical characteristic factor $h^i$ is, for example, the total molecular weight of the $i^{th}$ sample.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A system for measuring the heat energy of a combustible fluid comprising:
   means for directing radiation through a sample of the fluid;
   means for detecting the absorbance of at least one combustible component of the combustible fluid at a selected spectral line, there being at least one spectral line for each combustible component to be examined in the fluid;
   means for combining at least one heat energy proportionality factor with the absorbance at each spectral line; and
   means for summing said combinations to determine the heat energy of the fluid.

2. The measuring system of claim 1 in which said means for combining includes means for providing said proportionality factors, wherein each said heat energy proportionality factor relates one of said absorbances to at least one heat of combustion factor for the heats of combustion of one of each of at least one known standard, there being at least as many known standards as the number of said combustible components to be examined, each said component having a known heat of combustion, and wherein each said known standard includes at least one said combustible component.

3. The measuring system of claim 2 in which said means for providing includes a plurality of cells containing each combustible component to be examined in at least one of said cells, each said cell has a known standard including at least one said combustible component.

4. The measuring system of claim 3 in which there are at least as many cells as the number of selected spectral lines.

5. The measuring system of claim 3 in which each said cell contains some amount of each said combustible component.

6. The measuring system of claim 2 in which the heat energy proportionality factor is determined from the relationship $$P = \overline{HA}^t (\overline{AA}^t)^{-1}$$

wherein P is a matrix of heat energy proportionality factors $p_{kj}$, where k indicates one of 1 through K combustible components to be examined and j indicates one of 1 through N selected spectral lines;
wherein $\overline{A}$ is a matrix of absorbances $A_j^i$, where i indicates one of 1 through M known standards and j indicates spectral lines 1-N;
wherein $\overline{A}^t$ is the transpose of $\overline{A}$; and
wherein $\overline{H}$ is a matrix of heat of combustion factors $h_k^i$, where i indicates known standards 1-M and k indicates combustible components 1-K.

7. The measuring system of claim 6 in which said means for providing includes means for calculating said heat energy proportionality factors.

8. The measuring system of claim 6 in which said means for providing includes means for storing predetermined heat energy proportionality factors.

9. The measuring system of claim 6 in which $\overline{H}$ is a matrix of heat of combustion factors $h^i$, where i indicates known standards 1-M; and
P is a matrix of heat energy proportionality factors $p_j$, where j indicates spectral lines 1-N.

10. The measuring system of claim 9 in which said means for providing provides one proportionality factor for the absorbance at each spectral line.

11. The measuring system of claim 1 in which said means for determining multiplies each absorbance by the corresponding heat energy proportionality factor.

12. The measuring system of claim 1 in which said means for directing includes means for modulating said radiation at a predetermined frequency and means for synchronizing the detection of absorption with said frequency.

13. The measuring system of claim 1 in which said means for detecting measures absorption at at least one additional wavelength at which absorption by said combustible fluid is minimal.

14. The heat energy measuring system of claim 1 in which said means for directing emits wavelengths including infrared radiation.

15. The measuring system of claim 1 in which said means for detecting detects absorption at at least one spectral line for each $CH_x$ functional group of alkane hydrocarbons to be examined, where x is a number from 1 to 4.

16. The measuring system of claim 1 in which said means for detecting detects functional groups in a sample of combustible gas.

17. A system for measuring the heat energy of a combustible fluid comprising:
   means for detecting the absorbance of at least one combustible component of the combustible fluid at a selected spectral line, there being at least one spectral line for each combustible component to be examined in the fluid;
   means for combining at least one heat energy proportionality factor with the absorbance at each spectral line; and
   means for summing said combinations to determine the heat energy of the fluid.

18. A system for measuring a physical property of a fluid dependent on a physical characteristic of at least one functional group and related to the quantity of that functional group in the fluid comprising:
   means for directing radiation through a sample of the fluid;
   means for detecting the absorbance of at least one functional group of the fluid at a selected spectral line, there being at least one spectral line for each functional group to be examined in the fluid;
   means for combining at least one proportionality factor with the absorbance at each spectral line; and
   means for summing said combinations to quantify said dependent physical property of the fluid.

19. The measuring system of claim 18 in which said means for combining includes means for providing said proportionality factors, wherein each said proportionality factor relates one of said absorbances to at least one factor representing the physical characteristics of one of each of at least one known standard, there being at least as many known standards as the number of said functional groups to be examined, each said functional group having a known physical characteristic, and wherein each said known standard includes at least one said functional group.

20. The measuring system of claim 19 in which said means for providing includes a plurality of cells containing each said functional group to be examined in at least one of said cells, each said cell has a known standard including at least one said functional group.

21. The measuring system of claim 20 in which there are at least as many cells as the number of selected spectral lines.

22. The measuring system of claim 20 in which each said cell contains some amount of each said functional group.

23. The measuring system of claim 19 in which said proportionality factors are determined from the relationship $$P = \overline{HA'}(\overline{AA'})^{-1}$$

wherein P is a matrix of proportionality factors $p_{kj}$, where k indicates one of 1 through K functional groups to be examined and j indicates one of 1 through N selected spectral lines;

wherein $\overline{A}$ is a matrix of absorbances $A_i{}^j$, where i indicates one of 1 through M known standards and j indicates spectral lines 1-N;

wherein $\overline{A'}$ is the transpose of A; and wherein $\overline{H}$ is a matrix of physical characteristic factors $h_k{}^i$, where i indicates known standards 1-M and k indicates functional groups 1-K.

24. The measuring system of claim 23 in which said means for providing includes means for calculating said proportionality factors.

25. The measuring system of claim 23 in which said means for providing includes means for storing predetermined proportionality factors.

26. The measuring system of claim 23 in which $\overline{H}$ is a matrix of physical characteristic factors $h^i$, where i indicates known standards 1-M; and P is a matrix of proportionality factors $p_j$, where j indicates spectral lines 1-N.

27. The measuring system of claim 26 in which said means for providing provides one proportionality factor for the absorbance at each spectral line.

28. The measuring system of claim 18 in which said means for determining multiplies each absorbance by the corresponding proportionality factor.

29. The measuring system of claim 18 in which said means for directing includes means for modulating said radiation at a predetermined frequency and means for synchronizing the detection of absorption with said frequency.

30. The measuring system of claim 18 in which said means for detecting measures absorption at at least one additional wavelength at which absorption by the fluid is minimal.

31. The heat energy measuring system of claim 18 in which said means for directing emits wavelengths including infrared radiation.

32. The measuring system of claim 18 in which said means for detecting detects absorption at at least one spectral line for each $CH_x$ functional group of alkane hydrocarbons, to be examined, where x is a number from 1 to 4.

33. A system for measuring a physical property of a fluid dependent on a physical characteristic of at least one functional group and related to the quantity of that functional group in the fluid, comprising:

means for detecting the absorbance of at least one functional group of the fluid at a selected spectral line, there being at least one spectral line for each functional group to be examined in the fluid;

means for combining at least one proportionality factor with the absorbance at each spectral line;

said means for combining including means for providing said proportionality factors, wherein each said proportionality factor relates one of said absorbances to at least one factor representing the physical characteristics of one of each of at least one known standard, there being at least as many known standards as the number of said functional groups to be examined, each said functional group having a known physical characteristic, and wherein each said known standard includes at least one said functional group; and means for summing said combinations to quantify said physical property of the fluid.

34. A method of measuring the heat energy of a combustible fluid comprising:

directing radiation through a sample of the fluid;

selecting at least one spectral line for each combustible component to be examined;

detecting the absorbance of at least one combustible component of the fluid at each selected spectral line;

providing a heat energy proportionality factor between the absorbance at each selected spectral line and a heat of combustion factor for a known standard including at least one combustible component to be examined, there being at least one known standard for each combustible component;

combining each heat energy proportionality factor with the absorbance at each spectral line; and summing the combinations to determine the heat energy of the combustible fluid.

35. A method of measuring a physical property of a fluid dependent on the physical characteristics of at least one functional group and related to the quantity of that functional group in the fluid comprising:

directing radiation at a sample of the fluid;

selecting at least one spectral line for each functional group to be examined;

detecting the absorbance of at least one functional group of the fluid at each selected spectral line;

providing a proportionality factor between the absorbance at each selected spectral line and a factor representing the physical characteristics of a known standard which includes at least one of functional group to be examined, the functional group having a known physical characteristic and there being at least one known standard for each functional group;

combining each proportionality factor with the absorbance at each spectral line; and summing the combinations to quantify the dependent physical property.

36. A system for measuring a thermodynamic property of a fluid dependent on a thermodynamic characteristic of at least one component and related to the quantity of that component in the fluid comprising:

means for directing radiation through a sample of the fluid;

means for detecting the absorbance of at least one component of the fluid at a selected spectral line, there being at least one spectral line for each component to be examined in the fluid;

means for combining at least one thermodynamic proportionality factor with the absorbance at each spectral line; and means for summing said combination to quantify said dependent thermodynamic property of the fluid.

37. The measuring system of claim 36 in which said dependent thermodynamic property is heat of vaporization.

38. The measuring system of claim 36 in which said dependent thermodynamic property is thermal conductivity.

39. The measuring system of claim 36 in which said dependent thermodynamic property is heat capacity.

* * * * *